(12) United States Patent
Lee et al.

(10) Patent No.: US 11,484,880 B2
(45) Date of Patent: Nov. 1, 2022

(54) MICRODEVICE FOR DETECTING ALDEHYDES OR KETONES

(71) Applicant: LG Chem, Ltd., Seoul (KR)

(72) Inventors: Gyeongjin Lee, Daejeon (KR); Byung Hyun Park, Daejeon (KR); Su Youn Han, Daejeon (KR); Byoung Hyoun Kim, Daejeon (KR)

(73) Assignee: LG Chem, Ltd.

( * ) Notice: Subject to any disclaimer, the term of this patent is extended or adjusted under 35 U.S.C. 154(b) by 148 days.

(21) Appl. No.: 16/763,094

(22) PCT Filed: Oct. 19, 2018

(86) PCT No.: PCT/KR2018/012426
§ 371 (c)(1),
(2) Date: May 11, 2020

(87) PCT Pub. No.: WO2020/004719
PCT Pub. Date: Jan. 2, 2020

(65) Prior Publication Data
US 2020/0360926 A1    Nov. 19, 2020

(30) Foreign Application Priority Data

Jun. 25, 2018  (KR) .................. 10-2018-0072922

(51) Int. Cl.
*B01L 3/00*          (2006.01)
*G01N 21/33*         (2006.01)

(52) U.S. Cl.
CPC ........ *B01L 3/502715* (2013.01); *G01N 21/33* (2013.01); *B01L 2300/0803* (2013.01); *B01L 2300/087* (2013.01); *B01L 2300/16* (2013.01); *B01L 2400/0406* (2013.01); *B01L 2400/0409* (2013.01)

(58) Field of Classification Search
CPC .. B01L 3/502715; B01L 3/5027; B01L 3/502; B01L 3/50; B01L 2300/0803; B01L 2300/087; B01L 2300/16; B01L 2400/0406; B01L 2400/0409; G01N 21/33;
(Continued)

(56) References Cited

U.S. PATENT DOCUMENTS

| 6,342,349 B1 | 1/2002 | Virtanen |
| 2008/0058991 A1 | 3/2008 | Lee et al. |

(Continued)

FOREIGN PATENT DOCUMENTS

| CN | 206441437 U | 8/2017 |
| JP | H11101791 A | 4/1999 |

(Continued)

OTHER PUBLICATIONS

Seo, English Machine Translation of Description of KE 2017-0017687 A1, obtained on Dec. 1, 2021, from epo.org, pp. 1-53. (Year: 2017).*

(Continued)

*Primary Examiner* — Christine T Mui
(74) *Attorney, Agent, or Firm* — Lerner, David, Littenberg, Krumholz & Mentlik, LLP (57) ABSTRACT

A device and system for detecting aldehydes or ketones and, more particularly, a device and system, for detecting aldehydes or ketones, utilized in a rotating platform are provided.

6 Claims, 7 Drawing Sheets

(58) Field of Classification Search
CPC ........ G01N 21/31; G01N 21/25; G01N 21/17; G01N 21/00
USPC .......... 422/502, 501, 50, 258, 256, 255, 155
See application file for complete search history.

(56) References Cited

U.S. PATENT DOCUMENTS

| | | |
|---|---|---|
| 2008/0233594 A1 | 9/2008 | Inganas |
| 2008/0293151 A1 | 11/2008 | Wada |
| 2010/0297659 A1 | 11/2010 | Yoo |
| 2011/0189701 A1 | 8/2011 | Kim |
| 2014/0109972 A1 | 4/2014 | Garcia Da Fonseca et al. |
| 2016/0038939 A1* | 2/2016 | Min .................. B01L 3/502738 422/506 |

FOREIGN PATENT DOCUMENTS

| | | |
|---|---|---|
| JP | 2007205867 A | 8/2007 |
| JP | 2014508952 A | 4/2014 |
| KR | 20110088746 A | 8/2011 |
| KR | 20130000009 A | 1/2013 |
| KR | 20140148194 A | 12/2014 |
| KR | 20170017687 A | 2/2017 |

OTHER PUBLICATIONS

Holdren, M. et al, Investigation of 2,4-Dinitrophenylhydrazine Impregnated Adsorbent Tubes for the Collection of Airborne Aldehydes, United States Environmental Protection Agency Project Summary, Aug. 1988, EPA/600/S4-88/022. (Year: 1988).*

Guglielmino, et al., "On-line gaseous formaldehyde detection by a microfluidic analytical method based on simultaneous uptake and derivatization in a temperature controlled annular flow," Talanta, Sep. 1, 2017, pp. 102-108, vol. 172.

International Search Report for Application No. PCT/KR2018/012426 dated Apr. 3, 2019, 2 pages.

Madavie, et al., "Development of a Paper-Based Approach for the Detection of Carbonyl Compounds in Indoor Air Samples," Sri Lankan J. Biol., Jun. 30, 2017, pp. 1-11, vol. No 2.

Weng, et al., "Rapid detection of formaldehyde concentration in food on a polydimethylsiloxane (PDMS) microfluidic chip," Food Chemistry, Jun. 1, 2009, pp. 1079-1082, vol. 114.

Extended European Search Report including Written Opinion for Application No. EP18924573.1 dated Jun. 4, 2020, 8 pgs.

* cited by examiner

MICRODEVICE FOR DETECTING ALDEHYDES OR KETONES

CROSS REFERENCE TO RELATED APPLICATION

The present application is a national phase entry under 35 U.S.C. § 371 of International Application No. PCT/KR2018/012426 filed Oct. 19, 2018 which claims priority from Korean Patent Application No. 10-2018-0072922 filed on Jun. 25, 2018, the disclosures of which are incorporated herein by reference in their entirety.

TECHNICAL FIELD

The present invention relates to a device and a system for detecting aldehydes or ketones, and more specifically, to a device and a system for detecting aldehydes or ketones using a rotatable platform.

BACKGROUND ART

Generally, aldehyde has no chromophore and UV detection is impossible. Therefore, it is common to conduct derivatization with an acetyl acetone reagent or a 2,4-dinitrophenylhydrazine (DNPH) reagent and then to detect the aldehyde using High Performance Liquid Chromatography (HPLC). The method using acetyl acetone is a derivatization method wherein the acetyl acetone selectively reacts with formaldehyde, and the method using DNPH is a method of analyzing DNPH derivatives produced by the reaction between carbonyl compounds and DNPH by reacting with the carbonyl compounds. For aldehydes and ketones existing in the air, commercially available DNPH cartridges are used. Since conventional methods require expensive equipment and skilled analytical techniques, it is difficult to perform analysis of aldehydes or ketones quickly and simply in the field.

DISCLOSURE

Technical Problem

It is required to develop an economical and cost-effective color development-based aldehydes and/or ketones analysis system for the replacement of an expensive aldehydes and/or ketones analysis equipment, and it is required to develop a miniaturized analysis system that can be conveniently applied in the field.

Further, it is required to develop a system capable of simultaneously detecting a plurality of samples including aldehydes and/or ketones and reducing the analysis time.

Technical Solution

The device for detecting aldehydes or ketones according to the present invention may comprise:

a disk-shaped rotatable platform; and a microfluidic structure disposed on the rotatable platform, which may comprise:

a sample injection part where a fluidic sample containing the aldehydes or ketones is injected and the aldehydes or ketones can be subjected to DNPH derivatization;

a first microfluidic channel (siphon channel) that is a passage through which the sample can move to a detection part and connects the sample injection part and the detection part;

an eluent introduction part into which an eluent can be injected;

a second microfluidic channel that is a passage through which the eluent can move to the detection part and connects the eluent introduction part and the detection part; and a detection part coated with a substance capable of causing reaction with the aldehydes or ketones of the sample so that the aldehydes or ketones of the sample can be separated and developed with the eluent, wherein upon rotation of the rotatable platform, the aldehydes or ketones injected into the sample injection part may be subjected to DNPH derivatization.

Further, in the device for detecting aldehydes or ketones according to the present invention, the aldehydes or ketones which can be contained in the sample may be at least one selected from the group consisting of acetaldehyde, acetone, acrolein, benzaldehyde, butyraldehyde, formaldehyde and propionaldehyde.

Further, in the device for detecting aldehydes or ketones according to the present invention, the inside of the sample injection part may be filled with 2,4-DNPH coated silica in the form of beads.

Further, in the device for detecting aldehydes or ketones according to the present invention, the microfluidic structure may be provided in a plurality, and the plurality of microfluidic structures can accommodate different fluidic samples, respectively, and may be disposed radially symmetrically on the rotatable platform.

Further, in the device for detecting aldehydes or ketones according to the present invention, the microfluidic structure may comprise a reserve area connecting the second microfluidic channel and the detection part, and one end of the detection part may be accommodated in the reserve area.

Further, in the device for detecting aldehydes or ketones according to the present invention, the microfluidic structure may further comprise: a first air circulation channel connecting the sample injection part and the other end of the detection part; and a second air circulation channel connecting the eluent introduction part and the other end of the detection part, wherein the first air circulation channel and the second air circulation channel may increase the evaporation rate of the fluidic sample and the eluent in the detection part and prevent moisture condensation in the detection part.

Further, in the device for detecting aldehydes or ketones according to the present invention, the first microfluidic channel and the second microfluidic channel may comprise bending parts, respectively, and the number of the bending part of the second microfluidic channel may be one more than the number of the bending part of the first microfluidic channel.

Further, in the device for detecting aldehydes or ketones according to the present invention, during the first rotation of the device, the injected fluidic sample may move to the rear end of the sample injection part, and the injected eluent may move to the rear end of the eluent introduction part;

upon stopping the device after the first rotation of the device, the sample may move from the sample injection part to the first microfluidic channel, and the eluent may move from the eluent introduction part to the first bending part of the second microfluidic channel;

during the second rotation of the device, the sample may be introduced from the first microfluidic channel to the detection part;

upon stopping the device after the second rotation of the device, the eluent may move from the first bending part of the second microfluidic channel to the second bending part of the second microfluidic channel;

during the third rotation of the device, the eluent may be introduced from the second microfluidic channel to the reserve area; and upon stopping the device after the third rotation of the device, the sample may be developed on the detection part by the eluent.

Further, a system for detecting aldehydes or ketones comprising: the device for detecting aldehydes or ketones according to the present invention, and a UV lamp for visually observing the aldehydes or ketones separated and developed on the detection part by irradiating UV to the detection part may be provided.

Advantageous Effects

According to the present invention, it is possible to provide an economical and cost-effective color development-based aldehydes or ketones analysis system as compared with an expensive HPLC which is a conventional aldehydes or ketones analysis equipment, and also to provide a miniaturized analysis system that can be conveniently applied in the field.

Further, according to the present invention, there is an advantage that it is possible to perform analysis by detecting a plurality of samples including aldehydes or ketones simultaneously, thereby shortening the analysis time.

BEST MODE CARRYING OUT THE INVENTION

Various changes in form and details may be made to the presently disclosed embodiment and thus should not be construed as being limited to the aspects set forth herein. The presently disclosed embodiment is not limited to the aspects described in the present description, and thus it should be understood that the presently disclosed embodiment includes every kind of variation example or alternative equivalent included in the spirit and scope of the presently disclosed embodiment. Also, while describing the aspects, detailed descriptions about related well-known functions or configurations that may diminish the clarity of the points of the aspects of the presently disclosed embodiment will be omitted.

The device for detecting aldehydes or ketones according to the present invention may comprise:

a disk-shaped rotatable platform; and a microfluidic structure disposed on the rotatable platform, which may comprise:

a sample injection part where a fluidic sample containing the aldehydes or ketones is injected and the aldehydes or ketones can be subjected to DNPH derivatization;

a first microfluidic channel (siphon channel) that is a passage through which the sample can move to a detection part and connects the sample injection part and the detection part;

an eluent introduction part into which an eluent can be injected;

a second microfluidic channel that is a passage through which the eluent can move to the detection part and connects the eluent introduction part and the detection part; and a detection part coated with a substance capable of causing reaction with the aldehydes or ketones of the sample so that the aldehydes or ketones of the sample can be separated and developed with the eluent, wherein upon rotation of the rotatable platform, the aldehydes or ketones injected into the sample injection part may be subjected to DNPH derivatization.

Further, in the device for detecting aldehydes or ketones according to the present invention, the aldehydes or ketones which can be contained in the sample may be at least one selected from the group consisting of acetaldehyde, acetone, acrolein, benzaldehyde, butyraldehyde, formaldehyde and propionaldehyde.

Further, in the device for detecting aldehydes or ketones according to the present invention, the inside of the sample injection part may be filled with 2,4-DNPH coated silica in the form of beads.

Further, in the device for detecting aldehydes or ketones according to the present invention, the microfluidic structure may be provided in a plurality, and the plurality of microfluidic structures can accommodate different fluidic samples, respectively, and may be disposed radially symmetrically on the rotatable platform.

Further, in the device for detecting aldehydes or ketones according to the present invention, the microfluidic structure may comprise the reserve area connecting the second microfluidic channel and the detection part, and one end of the detection part may be accommodated in the reserve area.

Further, in the device for detecting aldehydes or ketones according to the present invention, the microfluidic structure may further comprise: a first air circulation channel connecting the sample injection part and the other end of the detection part; and a second air circulation channel connecting the eluent introduction part and the other end of the detection part, wherein the first air circulation channel and the second air circulation channel may increase the evaporation rate of the fluidic sample and the eluent in the detection part and may prevent moisture condensation in the detection part.

Further, in the device for detecting aldehydes or ketones according to the present invention, the first microfluidic channel and the second microfluidic channel may comprise bending parts, respectively, and the number of the bending part of the second microfluidic channel may be one more than the number of the bending part of the first microfluidic channel.

Further, in the device for detecting aldehydes or ketones according to the present invention, during the first rotation of the device, the injected fluidic sample may move to the rear end of the sample injection part, and the injected eluent may move to the rear end of the eluent introduction part;

upon stopping the device after the first rotation of the device, the sample may move from the sample injection part to the first microfluidic channel, and the eluent may move from the eluent introduction part to the first bending part of the second microfluidic channel;

during the second rotation of the device, the sample may be introduced from the first microfluidic channel to the detection part;

upon stopping the device after the second rotation of the device, the eluent may move from the first bending part of the second microfluidic channel to the second bending part of the second microfluidic channel;

during the third rotation of the device, the eluent may be introduced from the second microfluidic channel to the reserve area; and upon stopping the device after the third rotation of the device, the sample may be developed on the detection part by the eluent.

Further, a system for detecting aldehydes or ketones comprising: the device for detecting aldehydes or ketones according to the present invention, and a UV lamp for visually observing the aldehydes or ketones separated and developed on the detection part by irradiating UV to the detection part can be provided.

MODE FOR INVENTION

Hereinafter, the device for detecting aldehydes or ketones using a rotatable disk system according to the present invention will be explained in detail. The accompanying drawings are provided for illustration only and should not be construed as limiting the scope of the invention.

In addition, the same or corresponding components are given by the same or similar reference numerals, regardless of the reference numerals in the drawings, for which the repeated explanation will be omitted, and for convenience of description, the size and shape of each illustrated structural member may be exaggerated or downsized.

Figure 1:
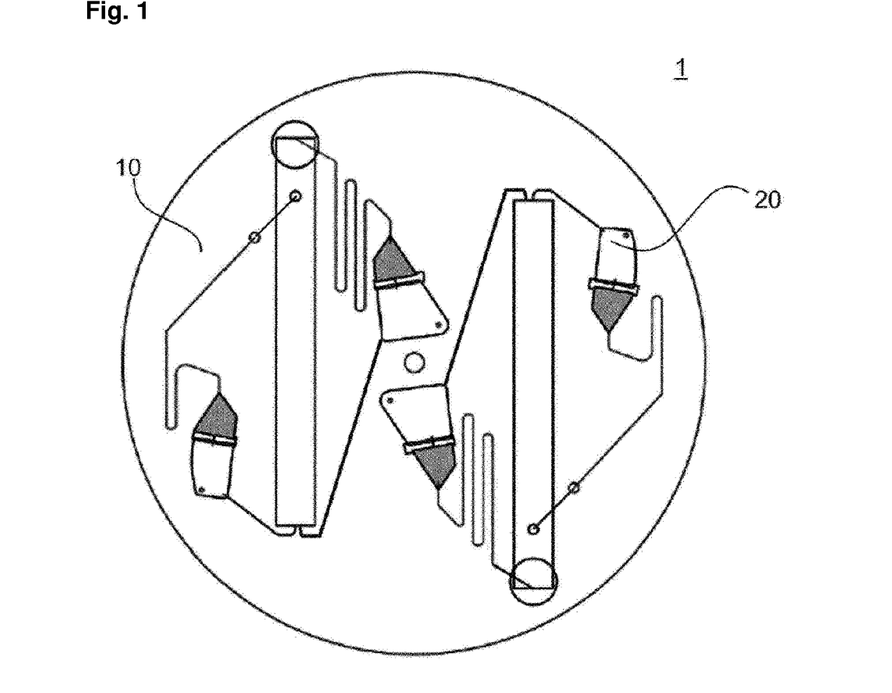
FIG. 1 illustrates the device for detection according to one embodiment of the present invention.
Figure 2:
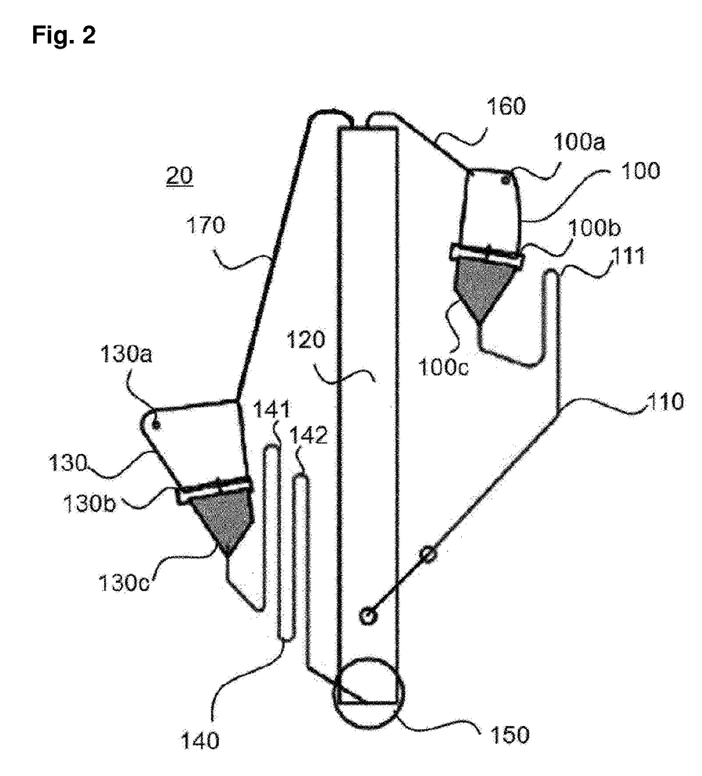
FIG. 2 illustrates a microfluidic structure of the device for detection of FIG. 1.

FIG. 1 illustrates the device for detecting aldehydes and/or ketones 1 according to one embodiment of the present invention, and FIG. 2 illustrates a microfluidic structure 20 of the rotatable disk system of FIG. 1.

First, referring to FIG. 1, the device for detecting aldehydes and/or ketones 1 comprises a rotatable platform 10 and a microfluidic structure 20 equipped in the rotatable platform 10. The rotatable platform 10 may be, for example, a circular disk, and its size may be, for example, 14 cm to 17 cm in diameter.

The rotatable platform 10 contains the microfluidic structure 20. The rotatable platform 10 may contain one microfluidic structure 20, or a plurality of microfluidic structures 20. The plurality of microfluidic structures 20 is disposed radially symmetrically on the rotatable platform 10. For example, FIG. 1 illustrates the case that two microfluidic structures 20 are disposed on the rotatable platform 10. Depending on the various circumstances in which the present invention is implemented, such as the size of the rotatable platform 10 and the plurality of microfluidic structures 20, three, four, five, six or more microfluidic structures can be disposed.

Referring to FIG. 2, FIG. 2 illustrates the microfluidic structure 20 of each of the plurality of microfluidic structures 20. The microfluidic structure 20 comprises: a sample injection part 100 where a fluidic sample containing the aldehydes or ketones is injected and a first microfluidic channel (siphon channel) 110 that is a passage through which the fluidic sample can move from the sample injection part 100 to a detection part 120, the detection part 120 that can separate and detect multiple aldehydes or ketones contained in the fluidic sample, an eluent introduction part 130, a second microfluidic channel 140 that is a passage through which the eluent can move from the eluent introduction part 130 to the detection part 120, and a reserve area 150 that connects the second microfluidic channel 140 and the detection part 120.

The microfluidic structure 20 can accommodate the fluidic samples containing a plurality of aldehydes and/or ketones and then can separate and detect the aldehydes and/or ketones. The aldehydes and/or ketones that can be contained in the fluidic sample may be, for example, at least one selected from the group consisting of acetaldehyde, acetone, acrolein, benzaldehyde, butyraldehyde, formaldehyde and propionaldehyde.

The sample injection part 100 has space to accommodate the fluidic sample containing aldehydes and/or ketones and contains an inlet 100a through which the fluidic sample can be injected into the space. In the sample injection part 100, 2,4-DNPH coated silica may be filled in the form of beads. Since aldehydes and/or ketones do not have a chromophore, the fluidic sample containing aldehydes and/or ketones is first subjected to DNPH derivatization in the sample injection part 100 before the fluidic sample containing aldehydes and/or ketones moves to the detection part 120.

The sample injection part 100 and the detection part 120 can be connected to the first microfluidic channel 110. Further, the sample injection part 100 can contain a blocking part 100b. The blocking part serves to trap the sample in the inner space of the sample injection part 100 using difference in level of the channel so that when the sample is injected through the inlet 100a, the injected sample is prevented from flowing directly to the first microfluidic channel 110. The blocking part 100b is provided with an opening part for moving the sample from the inlet 100a to the rear end part 100c of the sample injection part. By the first rotation of the rotatable platform 10, the sample moves from the inlet 100a to the rear end part 100c of the sample injection part. In the sample injection part 100, the rear end part 100c of the sample injection part, i.e., the vicinity of where the sample injection part 100 is connected to the first microfluidic channel 110, has a streamlined shape, for example. Accordingly, when the fluidic sample injected into the sample injection part 100 moves to the first microfluidic channel 110, the resistance is minimized so that the fluidic sample injected into the sample injection part 100 can completely move to the first microfluidic channel 110.

The first microfluidic channel 110 contains a bending part 111. The bending part 111 contains, for example, a "U" shaped tube part. As will be described later, upon stopping the device for detecting aldehydes and/or ketones 1 after the first rotation and before the second rotation of the detecting device 1, the fluidic sample containing DNPH-derivatized multiple aldehydes and/or ketones can move by the capillary force to the first microfluidic channel 110, which is hydrophilic inside the channel. As a result, the fluidic sample can be accommodated in the channel of the first microfluidic channel 110.

The end part of the first microfluidic channel 110 is connected to the detection part 120. The end part of the first microfluidic channel 110 may be located near the reserve area 150 so that the sample is provided from the first microfluidic channel 110 to the detection part 120 and the sample can be developed on the detection part 120 by the eluent provided in the reserve area 150 to be described later. However, the present invention is not limited to the above description, and various modifications are possible, for examples, the end part of the first microfluidic channel 110 can be connected to a part accommodated in the reserve area 150 of the detection part 120.

The detection part 120 can be coated with a substance that can react with the aldehydes and/or ketones of the fluidic sample to develop the fluidic sample. The detection part 120 may be, for example, RP-18 F254s TLC plate wherein a substance in which C18 group is bonded to silica is coated on an aluminum support to a thickness of 0.2 mm. The detection part may be coated with fluorescent detectable F254s, and water can be used up to 40%. The size of the detection part 120 may be, for example, 10 cm in length and 1 cm in width. This detection part 120 may be applicable to a small amount (e.g., 0.5 µL) of sample.

The eluent introduction part 130 has space to accommodate the eluent and the space contains an inlet 130a into which the eluent can be injected. The eluent introduction part 130 and the detection part 120 can be connected to the second microfluidic channel 140. Further, the eluent introduction part 130 may contain a blocking part 130b which serves to trap the sample in the inner space of the eluent introduction part 130 using difference in level of the channel so that when the sample is injected through the inlet 130a, the injected sample is prevented from flowing directly to the second microfluidic channel 140. The blocking part 130b is provided with an opening part for moving the eluent from the inlet 130a to the rear end part 130c of the eluent introduction part. By the first rotation of the rotatable platform 10, the eluent moves from the inlet 130a to the rear end part 130c of the eluent introduction part. In the eluent introduction part 130, the rear end part 130c of the eluent introduction part, i.e., the vicinity of where the eluent introduction part 130 is connected to the second microfluidic channel 140, has a streamlined shape, for example. Accordingly, when the fluidic sample injected into the eluent introduction part 130 moves to the second microfluidic channel 140, the resistance is minimized so that the fluidic sample injected into the eluent introduction part 130 can completely move to the second microfluidic channel 140.

The second microfluidic channel 140 contains at least two bending parts 141, 142. Each of the bending parts 141, 142 contains, for example, a "U" shaped tube part. The number of the bending parts 141, 142 of the second microfluidic channel 140 is one more than the number of the bending part 111 of the first microfluidic channel 110. This is because the sample is first introduced into the detection part 120 through the first microfluidic channel 110, and then the eluent is subsequently introduced into the detection part 120 through the second microfluidic channel 140. As will be described later, upon stopping the rotatable platform 10 after the first rotation and before the second rotation of the detecting device 1, the eluent can move by the capillary force to the hydrophilic second microfluidic channel 140. As a result, the eluent can be accommodated in the channel of the second microfluidic channel 140. More specifically, after the first rotation and before the second rotation, the eluent moves from the eluent introduction part 130 to the first bending part 141. Then, after the second rotation, the eluent moves from the first bending part 141 to the second bending part 142.

Further, the device for detecting aldehydes and/or ketones 1 contains a reserve area 150 at the end where the second microfluidic channel 140 is connected to the detection part 120, and one end of the detection part 120 is accommodated in the reserve area 150. The reserve area 150 is a concavely patterned area in the middle layer part and the bottom layer part of the rotatable platform 10 (see, FIG. 3a, FIG. 3c, FIG. 3d), respectively, so as to accommodate the eluent therein. After the first rotation of the rotatable platform 10, the eluent accommodated in the second microfluidic channel 140 moves from the second microfluidic channel 140 to the reserve area 150 during the third rotation of the rotatable platform 10, and at this time, the centrifugal force due to the rotation causes the eluent to be remained (i.e., trapped) in the reserve area 150 without being developed to the detection part 120. Upon stopping the third rotation of the rotatable platform 10, the eluent is developed to the detection part 120 connected to the reserve area 150, and the sample first introduced into the detection part 120 by the eluent is developed on the detection part 120 together.

Further, the device for detecting aldehydes and/or ketones 1 comprises the first air circulation channel 160 and the second air circulation channel 170. The first air circulation channel 160 connects between the sample injection part 100 and the other end part of the detection part 120. Accordingly, the components are connected in such a way that air circulates in the order of the sample injection part 100—the first microfluidic channel 110—the detection part 120—the first air circulation channel 160—the sample injection part 100. In the same manner, the second air circulation channel 170 connects between the eluent introduction part 130 and the other end part of the detection part 120. Accordingly, the components are connected in such a way that air circulates in the order of the eluent introduction part 130—the second microfluidic channel 140—the reserve area 150—the detection part 120—the second air circulation channel 170—the eluent introduction part 130.

By introducing the first air circulation channel 160 and the second air circulation channel 170, the evaporation rate of the fluidic sample and the eluent in the detection part 120 is increased while the moisture condensation in the detection part 120 is prevented. A capillary valve is formed by air pressure by drilling a hole with a thickness of about 1 mm and a diameter of about 0.8 mm at each of the points where the sample injection part 100 and the first air circulation channel 160 are connected and the eluent introduction part 130 and the second air circulation channel 170 are connected, so that backflow of the sample and the eluent to the first air circulation channel 160 and the second air circulation channel 170 can be prevented.

Figure 3A:
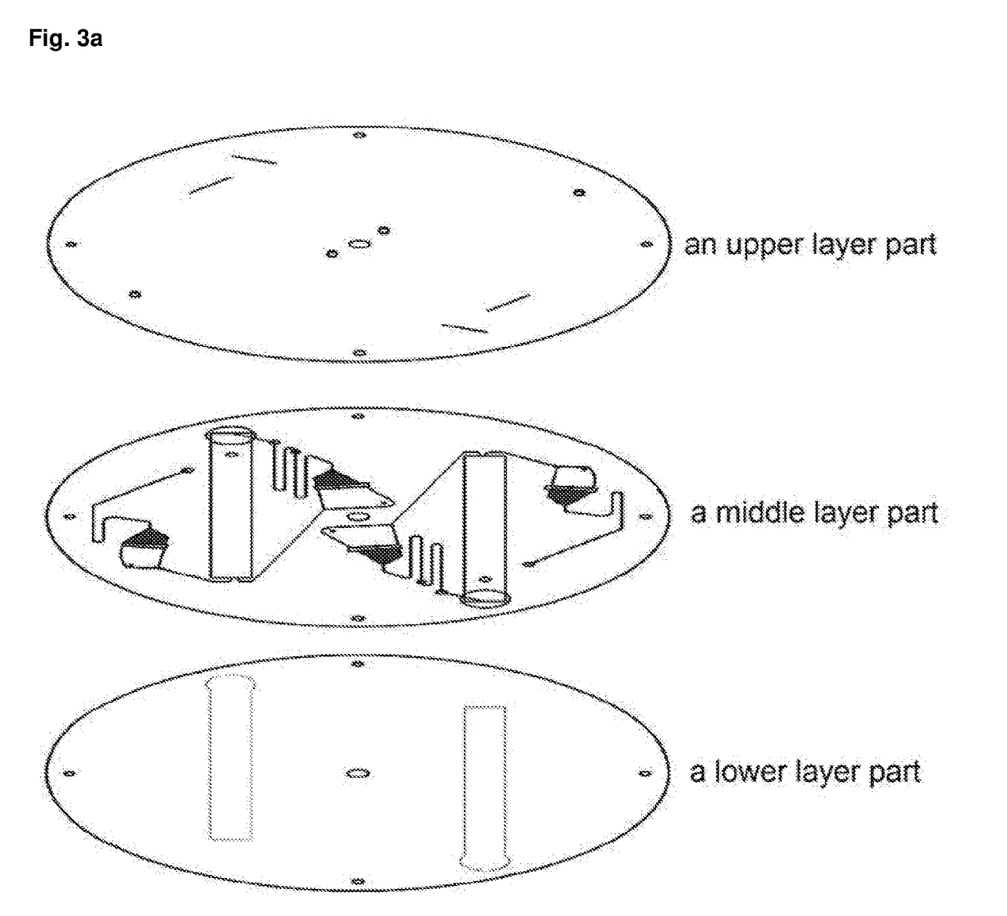
FIG. 3a to FIG. 3d illustrate each layer of a rotatable platform comprising a microfluidic structure.
Figure 3B:
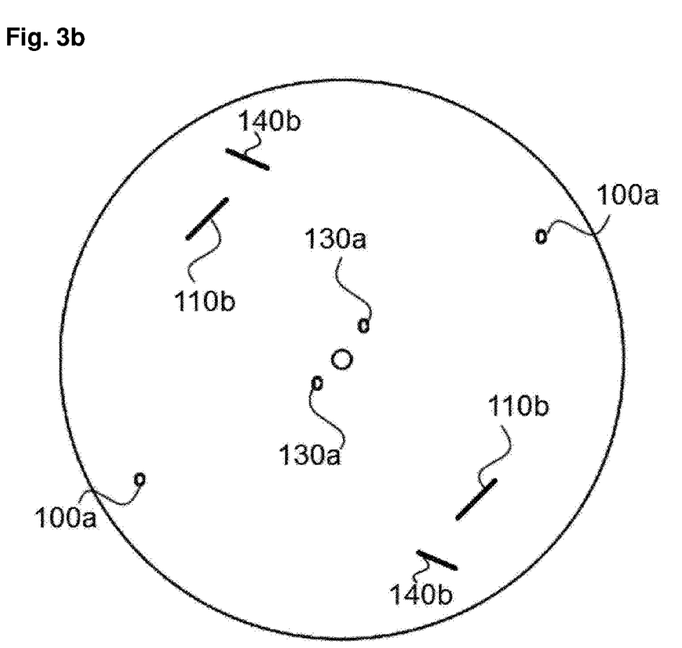
Figure 3C:
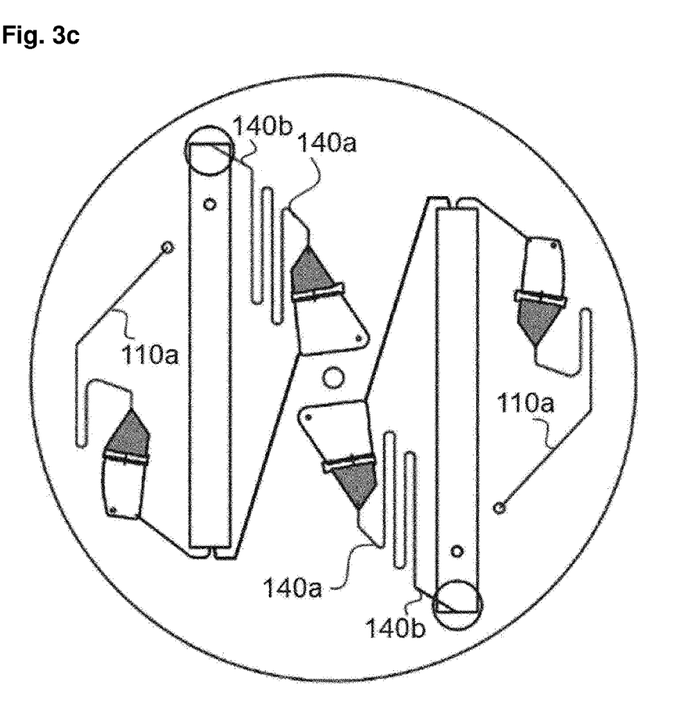
Figure 3D:
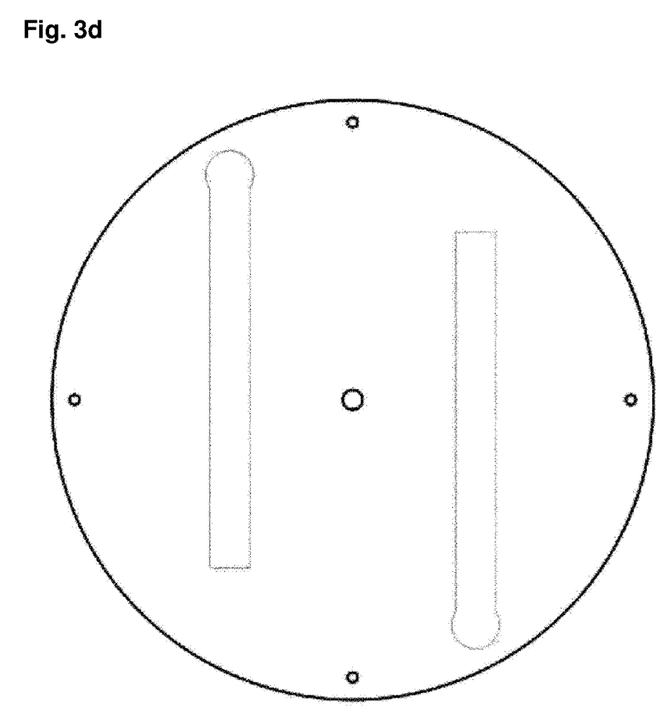

FIG. 3a to FIG. 3d illustrate each layer of the rotatable platform 10 containing the microfluidic structure 20 of FIG. 1. As shown in FIG. 3a, the rotatable platform 10 containing the microfluidic structure 20 can be composed of three layers, an upper layer part (FIG. 3b), a middle layer part (FIG. 3c) and a lower layer part (FIG. 3d). Each component of the microfluidic structure 20 except the detection part 120 can be formed by a patterning process using micro milling.

First, referring to FIG. 3a to FIG. 3c, the first part 110a of the first microfluidic channel 110 is disposed in the middle layer part, and the first part 110a includes a part connected to the sample injection part 100 and a bending part 111. The second part 110b of the first microfluidic channel 110 is disposed in the upper layer part, and the second part 110b includes a part connected to the detection part 120. This is to provide the sample in a manner that the sample falls down from the top of the detection part 120 in a downward direction, i.e., onto the detection part 120 when the sample is provided from the first microfluidic channel 110 to the detection part 120 after the sample is accommodated in the first part 110a of the first microfluidic channel 110 from the sample injection part 100 disposed in the middle layer. Accordingly, the sample can be developed more uniformly on the detection part 120.

The fluidic sample containing DNPH-derivatized multiple aldehydes and/or ketones is injected from the first microfluidic channel 110 located in the upper layer part of the rotatable platform 10 to the detection part 120 inserted in the middle layer part and the lower layer part of the rotatable platform 10, i.e., in a downward. Thus, the fluidic sample can be developed more uniformly on the detection part 120.

Further, referring to FIG. 3*a* to FIG. 3*c*, the first part 140*a* of the second microfluidic channel 140 is disposed in the middle layer part, and the first part 140*a* includes a part connected to the eluent introduction part 130 and bending parts 141, 142. The second part 140*b* of the second microfluidic channel 140 is disposed over the upper layer part and the middle layer part, and the second part 140*b* includes a part connected to the detection part 120. This is to allow the eluent to be introduced into the bottom center of the detection part 120.

Further, as shown in FIG. 3*b*, the upper layer part includes an inlet 100*a* of the sample injection part 100 and an inlet 130*a* of the eluent introduction part 130. As shown in FIG. 3*b* and FIG. 3*c*, the inlet 100*a* of the sample injection part 100 and the inlet 130*a* of the eluent introduction part 130 are formed over the upper layer part and the middle layer part. Thus, when the sample and the eluent are injected into the inlet 100*a* of the sample injection part 100 and the inlet 130*a* of the eluent introduction part 130 provided above the rotatable platform 10 (i.e., the upper layer part), respectively, the sample and the eluent are accommodated in the injection part 100 and the eluent introduction part 130 provided in the middle layer, respectively.

In the middle layer part, most of the components described above with reference to FIG. 1 and FIG. 2 are disposed. Therefore, the description overlapping with the components described in FIG. 1 and FIG. 2 with respect to the middle layer part will be described with reference to FIG. 1 and FIG. 2 described above.

Referring to FIG. 3*c* and FIG. 3*d*, a space that corresponds to the shape of the detection part 120 across the middle layer part and the lower layer part and into which the detection part 120 can be inserted, and the reserve area 150 through which one end of the detection part 120 can be inserted are provided. The middle layer part is opened to allow the detection part 120 to be inserted, and the lower layer part is provided with a concave portion that corresponds to the shape of the detection part 120 and in which the detection part 120 can be inserted. In the detection part 120 can be disposed over the middle layer part and the lower layer part. Further, the reserve area 150 is provided so that one end of the detection part 120 can be inserted over the middle layer part and the lower layer part. However, the present invention is not limited to the above description, and various modifications and changes are possible, for examples, the part where the detection part 120 is disposed in the upper layer part may be provided with a concave portion corresponding to the shape of the detection part 120 at the lower surface of the upper layer part so that the detection part 120 can be inserted.

Materials of the upper layer part, the middle layer part and the lower layer part may include, for example, polycarbonate (PC) or polymethylmethacrylate (PMMA) and the like.

On the other hand, an adhesive layer (not shown) is provided between the upper layer part, the middle layer part and the lower layer part to bond the upper layer part and the middle layer part, and the middle layer part and the lower layer part. The adhesive layer can be, for example, made of an acryl-based double-sided adhesive tape. In a tape of a plate made of a material having an adhesive component corresponding to the size of the rotatable platform 10, the regions corresponding to the above-described components of each layer part can be removed by, for example, cutting.

For example, in the adhesive layer bonding the upper layer part and the middle layer part, the region corresponding to the inlet 100*a* of the sample injection part 100 and the inlet 130*a* of the eluent introduction part 130 may be cut so that the sample and the eluent injected through the inlet 100*a* of the sample injection part 100 and the inlet 130*a* of the eluent introduction part 130 of the upper layer part, respectively, can move to the middle layer part. Further, in the adhesive layer bonding the middle layer part and the lower layer part, as shown in FIG. 3*a*, the regions corresponding to the components of the middle layer part and the lower layer part may be cut.

According to the detecting device 1 according to the present invention, by controlling the rotation of the device for detecting aldehydes and/or ketones 1, the fluidic sample containing aldehydes and/or ketones can move from the sample injection part 100 to the first microfluidic channel 110 and then to the detection part 120. Likewise, the eluent can move from the eluent introduction part 130 to the second microfluidic channel 140 and then to the detection part 120.

For example, after the fluidic sample containing aldehydes and/or ketones is injected into the sample injection part 100, when the detecting device 1 is rotated firstly at 3500 RPM for 20 seconds, the sample injected into the inlet 100*a* of the sample injection part 100 moves to a rear end part 100*c* of the sample injection part 100, and upon stopping of the detecting device 1 after the first rotation, the fluidic sample containing aldehydes and/or ketones moves from the rear end part 100*c* of the sample injection part 100 to the first microfluidic channel 110 by the capillary force. Further, during the first rotation, the eluent injected into the inlet 130*a* of the eluent introduction part 130 moves to the rear end part 130*c* of the eluent introduction part 130, and upon stopping of the detecting device 1 after the first rotation, the eluent moves to the first bending part 141 of the second microfluidic channel 140 by the capillary force.

Again, when the detecting device 1 rotates secondly at 3500 RPM for 20 seconds, the sample is introduced from the first microfluidic channel 110 to the detection part 120. Upon stopping of the detecting device 1 after the second rotation, the eluent moves to the second bending part 142 of the second microfluidic channel.

When the third rotation of the detecting device 1 proceeds at 1500 RPM for 20 seconds, the eluent is loaded on the reserve area 150, and after the third rotation of the detecting device 1 is stopped, the fluidic sample containing aldehydes and/or ketones is developed on the detection part 120 by the capillary force by the eluent.

Figure 4:
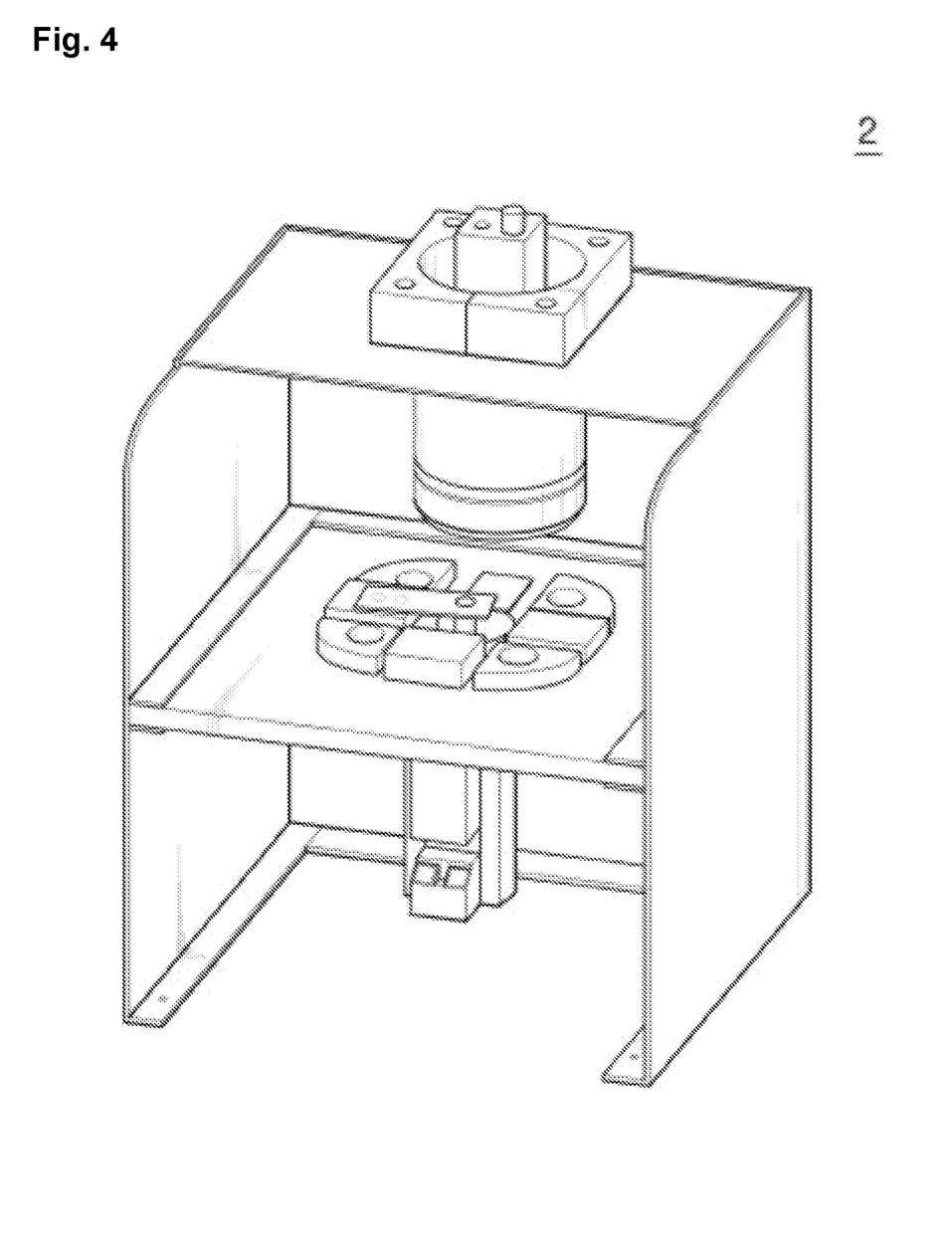
FIG. 4 illustrates a qualitative analytic system comprising the device for detection according to the present invention and capable of rotating the device.

FIG. 4 illustrates the system for detecting aldehydes and/or ketones 2 comprising the device for detecting aldehydes and/or ketones 1 according to the present invention. The system for detecting aldehydes and/or ketones 2 further comprises a UV lamp (not shown). The UV lamp may be installed, for example, on the underside of the ceiling part of the system for detecting aldehydes and/or ketones 2. However, the present invention is not limited thereto, and the position where the UV lamp can be installed can be variously modified and changed as long as the aldehydes and/or ketones sample developed on the detection part 120 can be visually confirmed by the irradiating the detection part 120 using the UV lamp. As described above, since the aldehydes and/or ketones do not contain a chromophore, it is developed on the detection part 120 after DNP derivatization in the sample injection part 100, and when the detection part 120 where the DNPH-derivatized aldehydes and/or ketones are developed is irradiated with the UV lamp, the aldehydes and/or ketones can be separated and detected visually.

Like this, by using the detecting device 1 according to the present invention, a plurality of aldehydes and/or ketones such as acetaldehyde, acetone, acrolein, benzaldehyde, butyraldehyde, formaldehyde and propionaldehyde can be qualitatively analyzed within 5 minutes. Since the seven kinds of aldehydes and/or ketones contained in the fluidic sample are developed differently on the detection part 120, the seven kinds of aldehydes and/or ketones developed on the detection part 120 can be detected, respectively, by irradiating the UV lamp 30 to the detection part 120.

According to the present invention, the DNPH derivatization of the aldehydes and/or ketones and their development on the detection part is accomplished by controlling the centrifugal force and capillary force by rotation control of the rotatable platform 10 on which the microfluidic structure 20 is placed.

Further, by using the detecting device 1 according to one embodiment of the present invention, it is possible to economically and rapidly separate and detect the multiple aldehydes and/or ketones. The device is more economical than the conventional expensive HPLC analysis equipment and can shorten the time required for analysis. Further, the device can be applied quickly and conveniently in the field where separation and detection of the multiple aldehydes and/or ketones is required. Moreover, if multiple samples are present and each of these samples contains different compositions of aldehydes and/or ketones, the multiple samples can be analyzed simultaneously in one device 1.

It should be understood that those skilled in the art can carry out other modifications without changing its technical spirit or essential features. Therefore, the above-described embodiment of the present invention is merely exemplary in all aspects and should not be construed to be limited, and it should be understood that the scope of the present invention is defined by the following claims and the meanings and ranges of the claims and all modifications and changed forms derived from their equivalents pertain to the scope of the present invention.

[Description of Symbols]
1: Device for detecting aldehydes and/or ketones
2: Analysis system for detecting aldehydes and/or ketones
10: Rotatable platform
20: Microfluidic structure
100: Sample injection part
110: First microfluidic channel
120: Detection part
130: Eluent introduction part
140: Second microfluidic channel
150: Reserve area
160: First air circulation channel
170: Second air circulation channel

The invention claimed is:

1. A device for detecting aldehydes or ketones comprising:
a disk-shaped rotatable platform; and
a microfluidic structure disposed on the disk-shaped rotatable platform, the microfluidic structure comprising:
a sample injection part configured to inject a fluidic sample containing aldehydes or ketones to subject the aldehydes or the ketones to DNPH derivatization, wherein an inside of the sample injection part is configured to be filled with 2,4-DNPH coated silica in the form of beads;
a first microfluidic channel having a passage configured to deliver the fluidic sample to a detection part and the first microfluidic channel having a first end in direct connection to the sample injection part and a second end in direct connection to the detection part;
an eluent introduction part configured to inject an eluent;
a second microfluidic channel having a passage configured to deliver the eluent to the detection part and the second microfluidic channel connects the eluent introduction part and the detection part;
a reserve area connecting the second microfluidic channel and the detection part and accommodating one end of the detection part;
a first air circulation channel connecting the sample injection part and the other end of the detection part;
a second air circulation channel connecting the eluent introduction part and the other end of the detection part;
and wherein the detection part is coated with a substance configured to react with the aldehydes or the ketones contained in the fluidic sample so that the aldehydes or the ketones is separated and developed by the eluent,
wherein upon rotation of the disk-shaped rotatable platform, the aldehydes or the ketones injected into the sample injection part are subjected to the DNPH derivatization,
wherein the disk-shaped rotatable platform is formed by stacking an upper layer part and a lower layer part,
wherein the eluent introduction part has space to accommodate the eluent and the space contains an inlet into which the eluent can be injected,
wherein the inlet of the eluent introduction part is formed on the upper layer part.

2. The device for detecting aldehydes or ketones according to claim 1, wherein the aldehydes or the ketones in the fluidic sample is at least one selected from the group consisting of acetaldehyde, acetone, acrolein, benzaldehyde, butyraldehyde, formaldehyde and propionaldehyde.

3. The device for detecting aldehydes or ketones according to claim 1, wherein the microfluidic structure is provided in a plurality, and
the plurality of microfluidic structures are configured to receive different fluidic samples, respectively, and the microfluidic structures are disposed radially and symmetrically on the disk-shaped rotatable platform.

4. The device for detecting aldehydes or ketones according to claim 1, wherein the first microfluidic channel and the second microfluidic channel comprises bending parts, respectively,
and a number of the bending part of the second microfluidic channel is one more than a number of the bending part of the first microfluidic channel.

5. The device for detecting aldehydes or ketones according to claim 1, wherein during a first rotation of the device, the injected fluidic sample moves to a rear end of the sample injection part, and the injected eluent moves to a rear end of the eluent introduction part;
upon stopping the device after the first rotation of the device, the fluidic sample moves from the sample injection part to the first microfluidic channel, and the eluent moves from the eluent introduction part to a first bending part of the second microfluidic channel;
during a second rotation of the device, the fluidic sample is introduced from the first microfluidic channel to the detection part;
upon stopping the device after the second rotation of the device, the eluent moves from the first bending part of the second microfluidic channel to a second bending part of the second microfluidic channel;

during a third rotation of the device, the eluent is introduced from the second microfluidic channel to the reserve area; and upon stopping the device after the third rotation of the device, the fluidic sample is developed on the detection part by the eluent.

6. A system for detecting aldehydes or ketones comprising the device for detecting aldehydes or ketones according to claim 1, and a UV lamp for visually observing the aldehydes or the ketones separated and developed on the detection part by irradiating UV radiation to the detection part.

* * * * *